(12) United States Patent
Puppels et al.

(10) Patent No.: US 8,688,384 B2
(45) Date of Patent: Apr. 1, 2014

(54) AUTOMATED CHARACTERIZATION AND CLASSIFICATION OF MICROORGANISMS

(75) Inventors: Gerwin Jan Puppels, Rotterdam (NL); Tom Bakker Schut, Zoetermeer (NL); Kornelis Maquelin, The Hague (NL)

(73) Assignee: River Diagnostics B.V., Rotterdam (NL)

( * ) Notice: Subject to any disclaimer, the term of this patent is extended or adjusted under 35 U.S.C. 154(b) by 919 days.

(21) Appl. No.: 10/556,365

(22) PCT Filed: May 11, 2004

(86) PCT No.: PCT/NL2004/000317
§ 371 (c)(1),
(2), (4) Date: Nov. 10, 2005

(87) PCT Pub. No.: WO2004/099763
PCT Pub. Date: Nov. 18, 2004

(65) Prior Publication Data
US 2007/0175278 A1   Aug. 2, 2007

(30) Foreign Application Priority Data
May 12, 2003   (EP) .................................... 03076420

(51) Int. Cl.
*G01N 33/48* (2006.01)
*G01N 31/00* (2006.01)
*G06G 7/48* (2006.01)
*G06G 7/58* (2006.01)

(52) U.S. Cl.
USPC .................... 702/19; 702/22; 703/11; 703/12

(58) Field of Classification Search
CPC ......... C12Q 1/00; A01N 2300/00; G01N 1/00
See application file for complete search history.

(56) References Cited

U.S. PATENT DOCUMENTS

| | | | |
|---|---|---|---|
| 5,112,745 A | 5/1992 | Lorr | |
| 5,424,959 A | 6/1995 | Reyes et al. | |
| 5,551,022 A | 8/1996 | Tariq et al. | |
| 5,573,927 A | 11/1996 | Nelson | |
| 5,866,430 A * | 2/1999 | Grow | 506/6 |
| 2002/0138210 A1* | 9/2002 | Wilkes et al. | 702/28 |

FOREIGN PATENT DOCUMENTS

EP   0 599 022   6/1994

OTHER PUBLICATIONS

Green et al., The role of environmental contamination with small round structured viruses in a hospital outbreak investigated by reverse-transcriptase polymerase chain reaction assay, Journal of Hospital Infection, 1998, 39, 39-45.*
Maquelin et al. (Journal of Clinical Microbiology, 2003, 41(1), 324-329).*

(Continued)

*Primary Examiner* — Larry D Riggs, II
(74) *Attorney, Agent, or Firm* — Young & Thompson

(57) ABSTRACT

An instrument, method, use and software program to obtain information rapidly about microorganisms that may spread uncontrolled in hospitals, water supply, food or when used in bio terrorism are described. Vibrational spectroscopy provides data to a computer linked to one or more databases. Comparison of the spectral data and information retrieved from the databases is used to identify and classify the microorganisms, applying suitable algorithms, which algorithms are self-generating and self-adapting to new spectroscopic data. The system may alert for the detection of an outbreak or to take disinfection measures. Changes in the traditional taxonomic division of microorganisms have no influence on the instrument. It does not rely on an a priori knowledge about the taxonomic classification of the microbial strain, is straightforward and easily integrated in routine microbial procedures.

14 Claims, 1 Drawing Sheet

(56) References Cited

OTHER PUBLICATIONS

Naumann D: "Infrared and NIR Raman Spectroscopy in Medical Microbiology" Proceedings of the SPIE, SPIE, Bellingham, VA, US, vol. 3257, 1998, pp. 245-257, XP002238946 ISSN: 0277-786X the whole document.

Greiser-Wilke I et al: "Structure and Presentation of a World Wide Web Database of CSF Virus Isolates Held at the EU Reference Laboratory" Veterinary Microbiology, Amsterdam, NL, vol. 73, 2000, pp. 131-136, XP002947398 ISSN: 0378-1135 the whole document.

Enright M C et al: "Multilocus Seqyence Typing" Trends in Microbiology, Elsevier Science Ltd., Kidlington, GB, vol. 7, No. 12, Dec. 1999, pp. 482-487, XP002947397 ISSN: 0966-842X the whole document.

Maquelin K et al: "Prospective Study of the Performance of Vibrational Spectroscopies for Rapid Identification of Bacterial and Fungal Pathogens Recovered From Blood Cultures" Journal of Clinincal Microbiology, vol. 41, No. 1, Jan. 2003, pp. 324-329, XP002253301 the whole document.

Schmitt J et al: "Artificial Neural Networks Applied to FTIR and FT-Raman Spectra in Biomedical Applications" American Institute of Physics, 1998, pp. 260-263, XP009034860.

Schmitt J et al.: "Stacked Spectral Data Processing and Artificial Neural Networks Applied to FT-IR and FT-Raman Spectra in Biomedical Applications", Proceedings of SPIE, vol. 3257, 1998, pp. 236-244.

\* cited by examiner

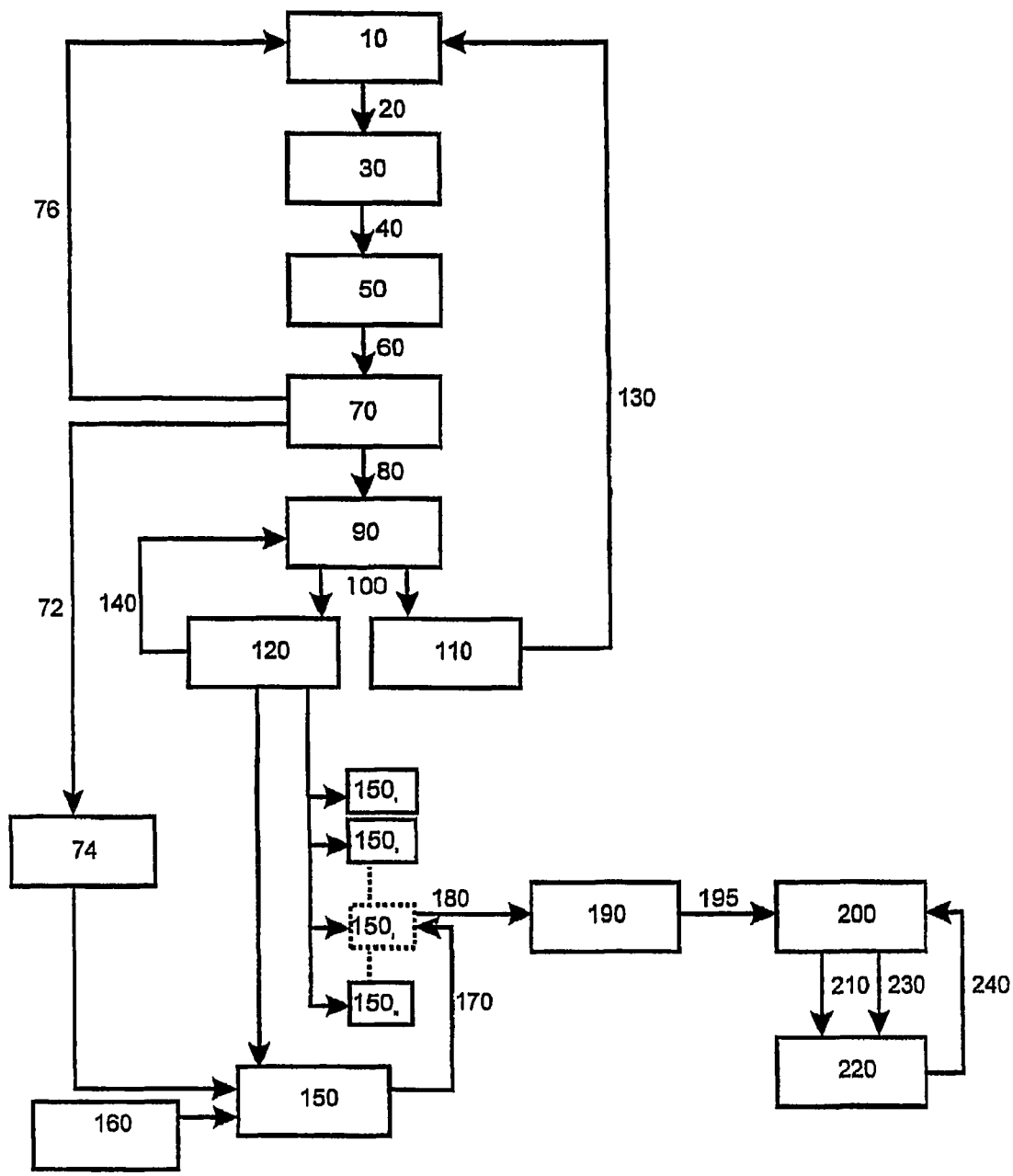

AUTOMATED CHARACTERIZATION AND CLASSIFICATION OF MICROORGANISMS

FIELD OF THE INVENTION

The present invention relates to an instrument and method for obtaining information about a microorganism in a sample of interest. In particular, it relates to obtaining information about microorganisms of interest using vibrational spectroscopy.

STATE OF THE ART

Microorganisms such as bacteria, fungi and viruses can do a lot of damage if they spread uncontrolled in food, hospitals, swimming pools, kitchens, water supply systems, air conditioning systems, or when they are used in bioterrorism. In such a situation it is of the utmost importance to stop the spread of the microorganism as quickly as possible by taking appropriate measures. Most of the time, these measures can only be taken if and after the microorganism responsible for the infection has been identified and if one is aware that infections show a certain pattern which requires further and immediate action.

Traditionally, identification was based on morphology, biochemical and nutritional properties, which is not reliable enough in situations in which public health is at stake since organisms that have been repeatedly transferred in the laboratory often do not retain their typical morphologic, biochemical or nutritional characteristics.

Many more sophisticated methods for the identification of microorganisms have been described over the last few decades.

U.S. Pat. No. 6,130,057 discloses a method for differentiating microorganisms in a sample utilizing a chromogenic indicator medium containing blood or hemin for growing and identifying microorganisms.

U.S. Pat. No. 4,847,198 discloses a method for the identification of microorganisms using UV excited Raman spectroscopy.

U.S. Pat. No. 6,177,266 discloses a method for the chemotaxonomic classification of bacteria with genus, species and strain specific biomarkers generated by matrix assisted laser desorption ionization time-of-flight mass spectrometry (MALDI-TOF-MS) analysis of either cellular protein extracts or whole cells.

In WO 02/20827, a system and method for performing real-time infection control is disclosed, which is based on the sequencing of DNA regions which are known to mutate not too fast and not too slow.

The above-mentioned methods and other state of the art methods have several disadvantages. For example, the methods generally are laborious, require expensive equipment and a high level of expertise from the person performing the experiments. It also takes too long, several days or weeks, before relevant information is obtained from the identification system and, last but not least, most of the identification and infection control systems rely on a well-defined taxonomy, without which identification, and thus infection control, is not possible.

Most of these disadvantages also apply to the method described in e.g. U.S. Pat. No. 5,112,745 and in Maquelin et al. 2003. U.S. Pat. No. 5,112,745 describes a method for identification of microorganisms based on infrared spectroscopy. Infrared spectra of known microorganisms are correlated with the results of other well established genotypic, phenotypic or other assays applied to the same known organisms. This requires the creation of a database of spectra and of results of well-established genotypic, phenotypic or other assays of known microorganisms. Using statistical analysis routines so-called "characterizing data" are then determined from the spectral signature. When a match is found between such characterizing data of an unknown microorganism and the characterizing data of a microorganism in the preexisting database of characterizing data of known microorganisms, the identification is established. These characterizing data serve to identify the microorganism or to extract other data from the microorganism, i.e. characterizing data from the infrared spectrum are used to predict the outcome of other assays that would otherwise be used to identify or otherwise characterize a microorganism.

Maquelin et al. ("Prospective study of the performance of vibrational spectroscopies for rapid identification of bacterial and fungal pathogens recovered from blood cultures" Journal of Clinical Microbiology vol. 41, pp. 324-329 (2003)) have used essentially the same approach to identify causative micoorganisms in bloodstream infections. First reference libraries of vibrational spectra of pathogens that are highly prevalent in blood stream infections were created, on the basis of which species-level identification models were developed using multivariate statistical analysis methods and artificial neural networks. The resulting models were then tested with spectra of newly isolated microorganisms and the results checked by means of routine well-established identification assays.

This approach in which spectroscopic features are correlated with the results of other assays, which serve as the gold standard, and in which it is attempted to obtain information about a microorganism directly from spectral features through such correlations, has several important disadvantages. To briefly mention just four of these disadvantages:

firstly, development of applications of the method requires extensive expertise and labor on the part of the user.

secondly, a spectrum of an unknown microorganism for which no match of characterizing data is found in the database cannot be used to extend the database in a way that automatically enables its use in the analysis of subsequently measured spectra, despite the fact that the spectrum may be sufficiently different from spectra of other microorganisms that it can serve as an identifier. An outbreak of a microorganism for which no match is found in the pre-existing database will not be noticed, and geographical spread or migration of a microorganism not represented in the pre-existing database cannot be monitored. This is a serious shortcoming e.g. in the light of possible acts of terrorism with biological agents or biological warfare and in the light of increasing problems with resistance to anti-microbial agents.

thirdly, if at any time the data with which the spectra have been correlated are revised, a recalculation of the correlations between spectra and the results of assays that are used as golden standard is required, which may affect the characterizing data that are extracted form the spectra. This is e.g. the case when changes are made in the classical taxonomic classification of a microorganism, by which it is classified as a different species than before, which frequently occurs.

fourth, in general microorganisms differ from each other in many aspects and not just with respect to the characteristic about which information is obtained by a particular assay, i.e. differences in spectral features are brought about by many different factors that affect the overall molecular composition of a microorganism. For example, it is not generally true, that vibrational spectra always show a high degree of correlation with genotypic or phenotypic assays. Closely related species or strains can have very different spectra, and in fact in some cases can more closely resemble strains from other species. This means that the method is limited to extracting characterizing data from the vibrational spectrum, which do show a high degree of correlation with the results of established assays.

This further underlines the need for a method which does not require prior taxonomic classification and which does not require a high level of expertise.

BRIEF DESCRIPTION OF THE FIGURE

The FIGURE shows an embodiment of the invention in which the instrument self generates an algorithm for establishing similarity between a spectrum from a sample of interest and samples in the database.

DETAILED DESCRIPTION

In a first aspect, the present invention relates to an instrument which comprises, a vibrational spectrometer, processing means, such as a computer, a first spectral database and a first information database, for obtaining information about a microorganism in a sample of interest by establishing vibrational spectroscopic similarity of the microorganism in the sample of interest to a vibrational spectrum stored in the first spectral database. The spectrometer, which is used for determining a vibrational spectrum of the microorganism in the sample of interest, is linked to the computer. The processing means, which in operation executes a computer program which comprises computer executable software code for analysis of the signal obtained from the spectrometer and for classification of the microorganism in the sample of interest, is linked to a spectrometer and to the databases. The first spectral database, which comprises vibrational spectra of microorganisms for establishing similarity of the spectrum of the microorganism in the sample of interest to the spectrum of a microorganism of which the spectrum is present in the first spectral database, is linked to the computer, and optionally to another database. This first spectral database may initially be empty and may conveniently be built up from scratch. The first information database, which comprises additional information about the microorganism of which the spectrum is present in the first spectral database, is linked to the computer, and optionally to another database. The instrument is characterised in that the spectroscopic similarity itself determines classification of the microorganism of interest and in that the spectrum of the microorganism in the sample of interest is used in the classification of subsequent spectra.

A first advantage of the instrument of the invention is that the user is not dependent on a well-defined taxonomy, because the system is based on the comparison of spectra, and the method of carrying out this comparison does not depend on traditional microbial taxonomy. Information about a microorganism in a sample of interest may be obtained by just comparing spectra without any attempt to relate measured spectra to traditional taxonomy. Microorganisms could simply be classified as belonging to spectroscopic cluster 1, 2, 3, . . . or N. It also means that any changes in the taxonomic division of microorganisms have no influence on the instrument of the invention. This is in contrast to state of the art fingerprinting techniques, because they rely on a priori knowledge about the taxonomic classification of the microbial strain. Of course, it is possible to identify at species and at subspecies level using the instrument of the invention, but it is not a prerequisite for obtaining useful information about the microorganism.

Another advantage is that the method of carrying out the comparison can be automatically updated to include a new spectrum that has been measured. Even if no further information is available about the strain of which the spectrum was obtained, its spectrum can be used to detect subsequent occurrences of the same strain.

Another advantage is that the use of vibrational spectroscopy for obtaining information about an unknown microbial strain is rapid, straightforward and easily integrated in routine microbial characterization procedures. In contrast to genotyping, vibrational spectroscopy would fit almost seamlessly into the daily routine of for instance a clinical microbiology laboratory. Moreover, the very limited or virtual absence of sample handling and the automated signal preprocessing and signal analysis also enables generation of user-specific subspecies fingerprinting databases, without requiring expertise beyond standard microbiological methods.

Another advantage is that the method of comparison of a new spectrum with spectra in a database is not limited to comparison with spectra in a local database. Because of the fact that spectra are measured and stored digitally they are immediately available for comparison with other databases too.

Identification of microorganisms using the instrument of the invention is very time efficient, since species and subspecies identification or sub-species relatedness of a new isolate to historical isolates in the database is all done on the basis of one simple, quick measurement which does not require any consumables for sample preparation or sample handling steps. It also does not require the manipulation of the environment of the microorganism in the sample, which would make the instrument unattractive for routine application.

The spectrometer of the instrument of the invention may be any type of vibrational spectrometer, i.e. an infrared (IR) spectrometer or a Raman spectrometer, which is known in the art.

Sample of Interest and its Preparation

A vibrational spectrum of the microorganism in the sample of interest is generally obtained after culturing the microorganism in the sample of interest under appropriate conditions for propagation. If convenient or required, the sample of interest is then transferred to carrier material, such as e.g. an aluminium foil or fused silica window. Depending on the vibrational technique which is used, suspensions may be standardised and inoculum density may be adjusted in order to obtain homogeneous films and reproducible results. However, in one embodiment cultures are subjected to spectrometry without sample preparation and are measured directly on their culture medium.

Typically, the microorganisms in the sample of interest are cultured by incubating the sample of interest in a suitable culture medium. The culture medium may be solid, which will result in colonies of biomass. The colonies are grown at a temperature which mimicks the situation at the place from which the sample of interest was taken, for many human pathogens this will typically be about 37° C., for a period which is long enough, typically about 4-8 hours, to obtain at least microcolonies. Microcolonies are colonies with a diameter of about 10-100 micrometer and a vibrational spectrum of microcolonies may be obtained in the instrument of the present invention while they are still on the solid culture medium. Larger colonies may be obtained by culturing for a longer period, e.g. about 16-24 hours. A vibrational spectrum from larger colonies may be obtained by streaking out part of the colony biomass on carrier material, creating a "smear". Even as little as one single cell may be used for obtaining a vibrational spectrum.

Alternatively, the culture medium may be a liquid culture medium. Microorganisms may be harvested from such liquid culture medium by methods known in the art, e.g. by centrifugation. The concentrated microorganisms may then be transferred to carrier material, optionally after drying, for obtaining a vibrational spectrum.

The sample of interest may be any kind of material including, but not limited to, patient material such as blood, urine, feces, intravenous catheters etc., industrial production lines, water systems, a food product, a cosmetic product, a pharmaceutical product and a forensic sample. Patient material is typically taken from and not returned to the patient. It may be taken from a living patient or it may be taken post-mortem. The microorganisms in the sample of interest may be any microorganism but preferably, a virus, a parasite, a bacterium, a yeast or a fungus. Most preferably, the microorganism in the sample of interest is a bacterium, a yeast or a fungus. This group includes well-known microorganisms such as *Acinetobacter, Bacillus, Bifidobacterium, Clostridium, Enterobacter, Escherichia, Lactobacillus, Lactococcus, Legionella, Listeria, Nitrobacter, Propionobacterium, Pseudomonas, Rhodobacter, Salmonella, Shigella, Staphyloccus, Streptococcus, Streptomyces, Candida, Saccharomyces, Aspergillus* and *Tychoderma*, but also new and not yet classified microorganisms.

In one embodiment, the microorganism is a member of any of the following genera: *Staphylococcus, Enterococcus, Mycobacterium, Acinetobacter, Streptococcus, Pseudomonas, Salmonella, Escherichia*.

Spectroscopy

Any type of IR spectroscopy may be used to obtain a vibrational spectrum, such as absorption/transmission, absorption/reflection, diffuse reflection and attenuated total reflection IR spectroscopy. In one embodiment, Fourier transform IR microspectroscopy is used. For IR microspectroscopy, suspensions of small amounts of microorganisms are typically cultivated on an appropriate nutrient agar plate, for e.g. about 16-24 hours at about 37° C. Small amounts of the microorganism are removed from the agar plate and suspended in distilled water and a droplet of the suspension is then transferred to a carrier. Spectra may be obtained from liquid solutions, suspensions or viscous or solid films which have been cast on a suitable carrier. Suitable carriers are IR-transparent plates which are water-insoluble and include materials such as $CaF_2$, $BaF_2$, ZnSe, ZnS and germanium. If a spectrum is obtained from a film, the droplet may be dehydrated in a desiccator over a drying agent, such as silica gel, under a moderate vacuum, to form a transparent film. The optical plate containing the microbial preparation is then sealed in a gas-tight cuvette cartridge and placed in the spectrometer. When spectra are obtained from microcolonies, diluted biomass suspensions are typically incubated for about 6-10 hours at about 37° C., before they are transferred from the agar nutrient plate to a suitable IR-transparent window. For IR spectroscopy on both colonies and microcolonies, suspensions are typically standardised and inoculum density is adjusted in order to obtain homogeneous films and reproducable results, although this may not always be strictly necessary. Preferably, the instrumental parameters are kept constant for all measurements which have to be compared. A suitable set of parameters would be a nominal physical resolution of between 1 and 15 $cm^{-1}$, and a sufficient number of scans to obtain a signal-to-noise ratio of between 1000:1 and 10000:1. In one embodiment, the nominal physical resolution is 6 $cm^{-1}$ and the signal-to-noise ratio is better than 3000:1.

Any type of Raman spectroscopy may be used to obtain a vibrational spectrum, such as ultraviolet (UV) resonance Raman spectroscopy, Fourier transform (FT) Raman spectroscopy and near infrared (NIR) multichannel Raman spectroscopy. In one embodiment, confocal Raman microspectroscopy is used. In general, Raman samples need less preparation than IR samples. There is e.g., no need for calibration or inoculum density adjustment. Typically, some biomass from microcolonies (6-10 hours at 37° C.) or from colonies (15-20 hours at 37° C.) is smeared on an optical substrate, such as $CaF_2$, and placed under the microscope. Alternatively, the samples may be air dried or dried in a desiccator and then be placed under the microscope. In an preferred embodiment, the samples are measured directly on the surface of the culture plate.

The sample is typically illuminated by a monochromatic light source with a line width sufficiently narrow to enable measurement of the desired Raman signal of a sample with sufficient spectral resolution, such as, e.g. a laser. Suitable lasers have an excitation power of greater than 50 mW to limit the signal collection time. For high laser powers the sample may be scanned through the laser focus during measurements or the laser beam may be scanned over the sample in order to distribute the laser power over a larger sample surface and thus prevent sample degradation. In one embodiment, an titanium sapphire laser delivering 100 mW of laser power is used.

A suitable excitation wavelength is at least 630 nm to avoid laser light induced damage to the sample and to minimise fluorescence scattering in the sample. In one embodiment, an excitation wavelength of 830 nm is used.

Although any Raman spectrometer may be used, a preferred option is a dispersive multi-channel spectrometer, such as e.g. a model 1000 from Renishaw plc, UK. Preferably, the detector is a multi-channel detector, such as for instance a charge coupled device (CCD) camera optimized with a light detection efficiency that is optimized for the near infrared region of the electromagnetic spectrum, in particular for the 700 to 1000 nm wavelength region.

The skilled person will understand that if other laser excitation wavelengths, e.g. in the deep UV, the visible region of the electromagnetic spectrum or further out in the near-infrared region of the electromagnetic spectrum, are used, also other detectors may be used, e.g. a multichannel detector may be employed with sensitivity in the near-infrared region beyond the region where a CCD-camera can be employed, e.g. a cooled InGaAs (indium gallium arsenide) multichannel detector. Alternatively, it may in some cases be beneficial to employ a Fourier-transform Raman spectrometer to analyze a Raman signal emitted in the near-infrared, in stead of a dispersive Raman spectrometer. The detector elements of the multi-channel detector may be calibrated for the wavenumber shift of the Raman signal incident on the detector elements. In one embodiment, this calibration is repeatable and reproducible to within 0.3 wavenumbers.

Typically several spectra from different positions in the sample are taken to cover all biochemical variation present. A suitable spectral range is that which covers wavenumber shifts from 250 $cm^{-1}$ to 2150 $cm^{-1}$. The skilled person will understand that a part or parts of this spectral range or other spectral regions may be employed too.

The relation between the wavenumber shift and the wavelength shift $\Delta cm^{-1}$ of a Raman signal with respect to the wavelength of the monochromatic light that is incident on the sample is given by:

$$\Delta cm^{-1}=100/\text{laserwavelength}(m)-100/\text{signalwavelength}(m)$$

The skilled person will understand that corrections have to be made for signal contributions form non-sample derived signal, including but not limited to signal from the optical substrate and/or the culture medium. The spectral resolution is typically better than 5 $cm^{-1}$, preferably better than 8 $cm^{-1}$ or wavenumbers.

Preferably the quality of the spectral signal is such that signal variance as a result of noise contributions is smaller than signal variance resulting from differences in molecular composition of microbial strains to be distinguished. For example, a signal to noise defined as the integrated signal intensity over the spectral region of 400 to 1800 wavenumbers, after subtraction of a straight baseline between these points, divided by the square root of this signal intensity, of 3200 was found to be sufficient to distinguish microbial strains isolated in 5 different outbreaks of infections by *Acinetobacter* strains. It will be clear to the skilled person that this number may be species-dependent and that it therefore may be advisable to measure spectra as a matter of standard with a signal-to-noise that is higher than 3200. Other methods of estimating the signal-to-noise may be applied.

The application of either vibrational spectroscopic technique to microorganisms is well-described in the art, e.g., in K Maquelin et al. pag-3308 In: Handbook of vibrational spectroscopy (2002) Eds. Chalmers & Griffiths.

After the spectra have been obtained, spectra are typically pre-processed, which comprises wavenumber calibration of the detection channels, and correction for the wavelength dependent signal detection efficiency of the instrument to obtain an instrument independent wavelength dependent signal detection efficiency. Suitable methods are known in the art, such as from R. Wolthuis et al, 1999, p. 431. In W. T. Mason (ed.), Fluorescent and luminescent probes for biological activity, 2nd ed. Academic press, London.

In one embodiment using Raman microspectroscopy, this is effected by substracting from all spectra the constant background signal contribution originating from optical elements in the laser light delivery pathway. Both the wavenumber and intensity axis of the spectra were calibrated. The wavenumber range which was projected on the camera was determined by measuring the spectra of two calibration lamps of which the absolute peak positions were known (e.g. a neon-lamp or a neon-argon-lamp) and one or more Raman standards of which the relative positions of the Raman peaks had been determined precisely (e.g. cyclohexane, 4-aceto-amidophenole). First a third order polynomial was fitted through the absolute calibration points (peak positions in nanometers as a function of the pixel numbers) to yield an absolute wavelength axis. Then the relative positions of the Raman peaks were used to calculate the exact laser wavelength. From the absolute wavelength axis and the laser wavelength the relative wavenumber axis was determined. This resulted in accuracy of the wavenumber axis of about a tenth of the pixel-width in wavenumbers, i.e. about 0.3 wavenumbers.

The reference spectrum of a tungsten band lamp of known temperature was used to correct for the wavelength dependent signal detection efficiency of the Raman set-up. The spectrum of the band lamp was calculated from Planck's radiation law and the emissivity of tungsten. The ratio of the measured spectrum and the calculated spectrum gave the instrument response profile which was used to correct all measured spectra. All spectra were then filtered using a 9-point Savitsky Golay filter, in which the first derivative of the spectrum is calculated. The spectral region between 400 and 1800 wavenumbers was used for data analysis. Finally each spectrum was scaled by subtracting the overall mean of the spectrum (i.e. the average signal of all spectral measurement channels) and dividing the spectrum by its overall standard deviation (a method commonly referred to as Standard Normal Variate scaling). Subsequently, the pre-processed spectra may be entered into the computer of the instrument of the invention The Processing Means and Classification Model The processing means, which will typically be a computer which, in operation, executes a computer program, is also part of the present invention. The computer may be a personal computer, or any other type of processing device, such as a single processor or multiprocessor system The program may be stored in a storage medium, such as, e.g., a floppy disk or CD-ROM which is read by a medium drive device such as, e.g., a floppy disk drive or a CD ROM drive. Alternatively, the program is stored in a storage medium forming part of the computer, such as e.g., a hard disk or other memory devices.

The computer program in operation executes computer executable software code for analysis of the signal obtained from the spectrometer and for classification of the microorganism. The analysis may be based on well known methods for developing algorithms which will enable a rapid search of the database to determine which spectrum or spectra in the database show the highest similarity with a new spectrum measured of an unknown microbial strain. Such algorithms may be developed by first applying, for example, principal component analysis, followed by linear discriminant analysis or hierarchical cluster analysis to the spectra in the database. This will organize the spectra in the database into clusters based on a measure of similarity between spectra. Such a measure may for instance be the squared Euclidean distance between spectra. Spectra within one cluster are more similar to each other than to any other spectrum in the database. Using a very powerful computer it would be feasible to perform a new cluster analysis with all spectra in the database and the newly measured spectrum of a microbial strains or spectra of a number of microbial strains, after which it is known which spectra of known microbial strains from the database are most similar to the new spectra.

Alternatively, first a classification model is developed based on a cluster analysis of the existing database of spectra of microbial strains. For example, a classification model is built by training an artificial neural network for separate branching points in the dendrogram that results from the clustering analysis. Of course other classification methods, such as but not limited to, linear discriminant analysis may be used instead of or in combination with artificial neural networks.

In one embodiment the classification model is spectroscopy guided. This means that the spectroscopic similarity between spectra itself is the input for development of the classification model.

This approach has an important advantage over approaches in which for instance the identity at genus, species and/or strain-level is the guiding principle for development of the classification model, because it does not suppose that a correlation exists between taxonomic relatedness and spectral similarity. This is not necessarily the case. For example, some species of *Enterococcus* contain carotenoids, whereas most others do not contain carotenoids. Carotenoids give an unusually strong and distinct contribution to the Raman spectrum and consequently in a cluster analysis such spectra come out as very dissimilar to spectra of other Enterococci and may in fact be more similar to spectra of other unrelated carotenoid containing strains.

Another advantage of the spectroscopy guided classification model is that it enables inclusion in the model of strains that have not yet been identified or characterized, other than by vibrational spectroscopy. Using spectroscopy guided classification, only a selected part of the spectrum will suffice in constructing the classification model. Different parts of the spectrum may be used at different steps.

All classification models may conveniently be combined with hierarchical cluster analysis. For example, the classification model may be used to limit the number of spectra to the spectra that are most similar to the new spectrum or spectra, after which as a final step a cluster analysis of this limited number of spectra from the database and the new spectrum may be performed to determine which spectrum or spectra in the database is most similar to the new spectrum. Based on spectral similarity found for the new strain and on known spectral similarities between spectra of microbial strains known to be different than the strain in the database that shows closest spectral similarity to the new strain, it may be decided that the new strain is the same as the strain already in the database and showing closest spectral similarity, or it may be decided that the new strain was not yet represented. An additional criterion may be to calculate if addition of the new spectrum to an existing cluster of spectra of a certain strain significantly increases the spectral variance within that cluster. If that is the case it may still be decided that the new spectrum belongs to a strain not yet represented in the database. If it is decided that the strain was already represented in the database, relevant information about this strain may be looked up in the information database. Other criteria may also be applied such as e.g. the inconsistency coefficient, which is a standard function in the statistics toolbox of MATLAB-programming software (The Mathworks inc, Natick, Mass., USA).

In another preferred embodiment, shown in FIG. 1, a dataset 10 of spectra measured with a vibrational spectroscopic technique and pretreated as described above was analyzed by means of principal component analysis (PCA) 20. Principal component analysis is an eigenvector decomposition of the covariance matrix of the spectral dataset. The software for this analysis and all subsequent analysis was programmed in Matlab 6.5 Release 13 (The Mathworks Inc., Natick, Mass., USA), using the PLS toolbox version 2.0 (Eigenvector Research Inc, Manson, Wash., USA).

The result 30 of this analysis was a collection of M−1 principal components (where M is the number of samples or the number of measurement points of the vibrational spectra, whichever is lower), and for each principal component an eigenvalue, which when divided by the sum of all eigenvalues, was the fraction of signal variance present in the dataset, that was represented by that principal component. The first $N_{PC}$ principal components, ranked according to eigenvalue, were used in further data-analysis. The number $N_{PC}$ was determined by applying a selection criterion 40 that includes all principal components that individually represent 1% or more of the signal variance in dataset 10, with a maximum of 10 principal components. The scores 50 of individual spectra on these $N_{PC}$ principal components were calculated as the inproduct of the spectrum with each of the $N_{PC}$ principal components. These scores were used as input for a hierarchical cluster analysis algorithm 60. The cluster analysis determines dissimilarity between spectra and/or clusters of spectra and partitions the spectral dataset into clusters 70 of similar spectra. Various measures of spectral dissimilarity may be applied. For example, Ward's algorithm may be used to calculate values of dissimilarity between spectra in a cluster. The dissimilarity value of a cluster is defined as the average squared Euclidean distance of all spectra belonging to that cluster to the spectrum that is obtained by averaging all spectra belonging to the cluster. Below a certain threshold-value of dissimilarity each spectrum in the database can be regarded as a separate cluster. By increasing this threshold, a value for dissimilarity is found above which 2 of the spectra are no longer regarded as dissimilar but as belonging to the same cluster. In this way for a database of $N_{sp}$ spectra $N_{sp}-1$ dissimilarity values (DV) may be found, defined such that between dissimilarity values DV(X) and DV(X+1) the database may be partitioned into X+1 clusters for values of X ranging from 1 to $N_{sp}-2$, and below dissimilarity value $DV(N_{sp}-1)$ the database may be partitioned into $N_{sp}$ clusters. In this way a partitioning matrix may be constructed in which the rows signify the partitioning levels, the columns signify the individual spectra and the matrix elements signify cluster-membership of a particular spectrum at a particular partitioning level. This partitioning was used as the basis for the development 80 of a Linear Discriminant Analysis (LDA) model 90, which classifies spectra according to cluster membership. The level of partitioning in the cluster analysis that was used as input for the development of an LDA-model was limited by imposing the criterion that the number of spectra in the smallest cluster was at least 2 times higher than the number of principal components $N_{PC}$ used in the cluster analysis. This was found to be a good method for avoiding overfitting of the spectral dataset in the development of the LDA-model. If the cluster analysis resulted in one or a number of clusters having fewer spectra than required by this criterion, even at the lowest partitioning levels (i.e. the partitioning level where the dataset is partitioned in only 2 or a few groups of spectra), these spectra were labeled as outliers 72, and added to a list of outlier spectra 74, and not further used in the development of the LDA-models. In such a case the search for a partitioning level at which clusters are found that all meet the above criterion for a minimum number of spectra, was repeated 76, starting with the spectral dataset 10 from which the outlier spectra were removed. An alternative approach is to repeat the cluster analysis with a reduced number of principal components in order to attempt to meet the criterion of the smallest cluster having a number of spectra that is 2 times higher than the number of principal components used. A validity test 100 of the LDA-model was carried out which tested the internal consistency of the LDA-model, meaning that each of the spectra used to create the LDA-model, was classified by the LDA-model. The criterion for model validity was that a 100% correct classification of spectra with respect to cluster membership was obtained.

If a valid LDA-model 110 was obtained, the entire procedure described above was repeated 130 for each cluster separately, with the spectra in the cluster serving as the spectral dataset 10.

If an invalid LDA-model 120 was obtained it was attempted to develop a valid LDA-model based on cluster membership of spectra at the next higher partitioning level in the cluster analysis results (i.e. the number of clusters into which spectra are classified was reduced by one) 140.

This procedure is continued until no more valid LDA-models can be developed that would further subdivide the initial spectral dataset 10. Also, no LDA-models are developed for subdivisions of the initial dataset 10 that contained fewer than 100 spectra.

Subdivisions of the initial dataset 10 for which valid LDA-models were obtained, were referred to as spectral subspaces.

Further subdivisions of spectral subspaces by hierarchical cluster analysis were referred to as clusters.

The end result of this automated procedure was a tree of LDA-models 150, with for each LDA-model the principal components that were used to generate that LDA-model, and a subdivision of spectra present in the starting spectral database 10 into spectral subspaces $150_1 \ldots 150_N$ for which valid LDA-models could be developed.

Moreover, for each spectrum in spectral subspaces $150_1 \ldots 150_N$ a reference dissimilarity value was determined. For determination of this value for spectra of a spectral subspace $150_i$ the results are used of a hierarchical cluster analysis carried out on the spectra of the spectral subspace $150_i$. The reference dissimilarity value was defined as the highest dissimilarity value of the cluster to which the spectrum belongs on condition that the cluster contains only spectra of the same strain. If the spectrum is not linked to a spectrum or group of spectra belonging to the same strain, the maximum dissimilarity level encountered in spectral subspace $150_i$ was adopted as reference dissimilarity value for that spectrum.

Subsequently the tree of LDA-models 150 was applied to the outlier spectra 72 listed in 74. For each LDA-model used in the classification the scores of an outlier spectrum 72 on the principal components, used to generate the LDA-model, were calculated after which the LDA-model was applied to the scores. The LDA-models enabled rapid determination 170 of which of these clusters $150_i$ was spectroscopically most similar to the outlier spectrum 72, after which the outlier spectrum was added to that cluster. The reference dissimilarity value that was assigned to the outlier spectrum was the maximum reference dissimilarity level of the cluster $150_i$.

In the same way the tree of LDA-models 150 enabled rapid determination 170 of the cluster $150_i$ which was spectroscopically most similar to a new spectrum 160, after which the new spectrum was added to that cluster.

When this was determined, the spectra in this cluster together with the new spectrum were subjected to a principal components analysis followed by a hierarchical cluster analysis (again using Ward's method) in which all principal components were used 180. When the new spectrum 160 of an isolate ended up in a cluster of spectra that were already in the database and that were obtained of a known strain, the identity 190 of the microorganism was established by virtue of spectroscopic similarity. This identity was then used to look up in information database 200 the available information about that strain, which was then presented 210 to the user 220. Database 200 contains information about the strains of which spectra are present in the spectral database 10, e.g. antimicrobial agent susceptibility, virulence, known complications, etc. The method that was used to determine cluster-membership of a new spectrum used the partitioning matrix generated by the hierarchical cluster analysis and started at the highest partitioning level in which all spectra belong to a separate cluster. From there the partitioning level was decreased step by step. At each step it was checked whether the new spectrum was clustered with another spectrum or cluster of spectra. If the new spectrum was clustered with a cluster of spectra belonging to different strains it was classified as an unknown strain. The strain received a unique code-name, and the user was prompted, e.g. visually and/or audible and/or by an electronic message 230, to enter available information 240 about this strain into the information database 200. This information may comprise e.g. the results of other techniques for microorganism identification, which may be phenotypic or genotypic and at any taxonomic level, an antibiogram, date of isolation, patient material from which the microorganism was isolated, and clinical complications caused by the infection.

At all times it is possible for the user to update the information database when new information about a strain becomes available, from whatever source. This may include information obtained by electronically linking and comparing information databases at regular intervals. If the new spectrum was clustered with one spectrum of a strain S, or a group of spectra that were all obtained of the same strain S, then the reference dissimilarity value of the nearest neighbor of the new spectrum was used to determine if the isolate from which the new spectrum was obtained was identified as strain S or not. If the dissimilarity value of this cluster including the new spectrum was less than 2 times this reference dissimilarity value, then the isolate of which the new spectrum was obtained was identified as strain S, and all information about strain S, which was stored in the information database 200 became available and information about the isolate from which the new spectrum was obtained was added to the information database. If the dissimilarity value of the sub-cluster including the new spectrum was more than 2 times the reference dissimilarity value, the strain of which the new spectrum was obtained was classified as unknown and received a unique code-name 195 under which information about this strain could be stored in information database 200. The user was prompted 230 to provide available information 240 about this strain into the information database 200. If spectroscopic similarity of the new spectrum with a spectrum or a cluster of spectra was established, the reference dissimilarity value of this spectrum or spectra was assigned to the new spectrum, otherwise it was assigned the maximum reference dissimilarity value of the spectral subspace $150_i$ to which it was spectroscopically most similar as determined by the LDA-models.

However, all new spectra 160 were immediately added to the cluster of spectra $150_i$ with which they shared the greatest spectroscopic similarity. In this way, they were immediately available to aid in identification of subsequent new isolates. Any outbreak of an organism may be determined in this way on the basis of spectroscopic similarity, even if the microbial identification has not yet been established.

The dataset of spectra available to serve as reference for newly measured spectra may continually and automatically be expanded with another measured spectrum. At regular intervals or e.g. after a predetermined number of new spectra had been added to the database, the whole procedure as described above may be repeated to enable creation of a new. LDA-tree which incorporates the spectral variance added to the spectral dataset by spectra added to the dataset after creation of the existing LDA-tree.

It is noted that the above embodiment for automated generation and automated updating of a database and its use in analyzing new spectra, is given only by way of example. It will be clear to those skilled in the art that choices for criteria that are applied and signal analysis methods that are used, can be replaced by alternatives.

The spectral database of the instrument of the invention thus comprises pre-processed spectra from the spectrometer which have been classified according to known or new classification models. Preferably, the spectroscopy guided classification model is used for the organisation of the database. The database is automatically adapted or extended by the incorporation of new spectra. It may comprise microbial spectra of subspecies specificity.

Instead of being linked to a first spectral database, the computer may, in operation, be executing an algorithm based on the first spectral database. This is an alternative way of establishing similarity of the spectrum of the microorganism in a sample of interest and the spectrum of a microorganism of which the spectrum is present in the first spectral database.

The Information Database

More information about the spectra in the spectral database may be obtained from the information database to which the spectral database may optionally be connected.

Connections between the first spectral database and other databases may be established by any means of data-transfer and suitable data-transfer protocols, including but not limited to wireless datatransfer, intranet systems, internet, the use of portable data storage devices such as computer diskettes and compact disks. The information database of the instrument of the invention comprises strain specific information comprising but not limited to prevalence, virulence, clinical complications, antimicrobial agent susceptibility, becomes instantly available. Moreover such information may be updated with the sample and/or patient information of the new sample of which the spectrum was obtained. Such information includes, but is not limited to, the time and date the patient material was obtained, the type of patient material used, the clinical condition of the patient and or the changes in the clinical condition of the patient, treatments, including the treatment for the infection and the effect thereof, diagnostic procedures that the patient has undergone, whether or not the infection has manifested itself after the patient was admitted to a hospital, antimicrobial agent susceptibility profile of the microbial strain, whether the microbial strain is or has been involved in an outbreak, virulence of the microbial strain, whether the isolated microbial strain is locally endemic (pointing to persistent source(s) of contamination), wards and departments where a patient has stayed or has been examined, taxonomic classification by other methods (including classification at genus, species and/or sub-species level), such as for instance 16S RNA sequencing, and other methods.

The first information database may be coupled to other databases, such as to a spectral database.

In this way, the instrument of the invention allows for sub-species level specific information to be obtained from a microbial strain. It also provides rapid access to useful clinical data such as best course of treatment, know complications of an infection with the particular strain and e.g. virulence of the microorganism. At the same time it provides information regarding earlier cases of infection with the same strain. This allows for the rapid determination of re-infection of a patient with the same strain, which is important as it may point to the existence of a source of the infection that is not eliminated by antimicrobial treatment, such as for instance an indwelling medical device, which requires additional measures to be taken. This is detected automatically, without requiring a previous suspicion of such re-infection, and without any requirement for further other tests.

In another preferred embodiment, the spectral database or algorithm based on this spectral database, and the information database are combined in one single database.

In another aspect, the instrument of the invention further comprises a second spectral database and a second information database. This second spectral database may comprise spectra which are not present in the first spectral database and the second information database may comprise additional information about the microorganisms in the second spectral database.

Networks

The instrument of the invention may be part of a network, such as a local, regional or global area network. The term "network", refers to two or more computers or processing systems which are connected in such a way that messages and information may be transmitted between the computers. In such computer networks, typically one or more computers operate as a "server", a computer with large storage devices such as hard disk drives and communication hardware to operate peripheral devices such as printers or modems. Other computers, termed "workstations" or "clients", provide a user interface so that users of computer networks may access the network resources, such as shared data files, common peripheral devices, and inter-workstation communication. Users activate computer programs or network resources to create "processes" which include both the general operation of the computer program along with specific operating characteristics determined by input variables and its environment. The network will comprise at least one server and at least one, and typically several workstations. Server and workstations are connected by a communication line, which may be an ethernet cable or another suitable device, such as a wireless connection. The network may also include several shared peripheral devices. In one embodiment of the invention, the spectrometer of the invention is a remote facility which is connected to the computer by a server.

A local, regional or global network of instruments may be suitably used to monitorgeographical presence and changes therein of microbial strains. It may automatically issue an alert if an unusual change in geographical presence has been detected. Unusual changes include, but are not limited to the prevalence of a new strain. Such network also allows for obtaining retrospectively epidemiological data without the requirement to do additional testing. In addition, it is possible to prospectively assemble epidemiological data. There is no need to know on forehand which vibrational spectra of which samples will be of later interest.

An instrument further comprising a signal which is or can be made visible or audible output in one or more of the following categories:

prompting the user that the vibrational spectrum of the microorganism in the sample of interest is already present in the first spectral database prompting the user to apply other means of characterisation, prompting the user to enter information in a second information database suggesting suitable antimicrobial therapy alerting the user to a change in antimicrobial agent susceptibility profile alerting the user to the existing of an outbreak alerting the user of a persisting contamination.

alerting the user when an unusual change in geographical presence occurs is also part of the invention.

Applications of the Invention

In another aspect, the invention provides for a method for obtaining information about a microorganism in a sample of interest comprising the following steps:

(a) using a vibrational spectrometer according to the invention to obtain a vibrational spectrum of subspecies specificity of the microorganism in a sample of interest;

(b) adding the spectrum of the microorganism in a sample of interest to a first database of spectra of microorganisms which may comprise zero or more spectra, and which first database is in a storage medium that can be accessed by a processing means, such as a computer;

(c) adding information about the microorganism in a sample of interest to a first information database. The type of information which may be added includes time and place of isolation, and information about the patient from which the sample of interest was isolated. The first information database contains information about microorganisms of which spectra are already present in the first spectral database. If there are no spectra in the first spectral database yet because this database is built up from scratch, then of course there will be no information in the first information database;

(d) using a processing means, such as a computer, which executes a self generating algorithm, which self adapts to new entries into the first spectral database, to determine to which spectrum or spectra in the first spectral database, the spectrum of the unknown microorganism bears greatest spectral similarity;

(e) applying criteria to determine if this spectral similarity is sufficient to conclude that the microorganism in the sample of interest is the same microorganism strain of which a spectrum is already present in the first spectral database;

(f) looking up information about the microorganism strain in the sample of interest in the first information database in case it was concluded in step (e) that spectral similarity between the microorganism in the sample of interest and a spectrum or spectra in the first database was sufficient. The first information database contains information about the microorganism strains of which spectra are included in the first spectral database, such information includes information about the identity of the microbial strain as determined by other means, the sensitivity of the microbial strain to certain antimicrobial agents, time and place of previous isolation of the microbial strain, clinical complications previously observed during or after infections caused by the microbial strain and information about the patient from which the microbial strain was isolated;

(g) reporting that no information is available regarding the microorganism in the sample of interest if no sufficient spectral similarity is found to a spectrum already in the first spectral database, whereby (b) and (c) may be performed before or after (e).

In yet another aspect, the invention provides for a method for disinfection of an object surface or solution. In this way for example a whole hospital or production facility may be disinfected, but also smaller areas, such as furniture and clothes. The method may also be used to disinfect parts of the human or animal body. The method comprises running a vibrational spectrum of a sample of interest on a instrument of the invention and taking disinfection measures based on the information from the instrument. A sample may be taken at different locations and at different times. In that case, if samples contain the same strain, a path of contamination may be established. The effects of the disinfection measures may be fed into an information database for future reference. There is no need for taxonomic classification of the microorganism(s) involved prior to disinfection.

In yet another aspect, the invention provides for a method for determining a nosocomial infection without the need for prior suspicion of a nosocomial (hospital acquired) infection and without the need for prior taxonomic classification of the microorganism(s) in the sample of interest. The method comprises classifying a microorganism in a sample of interest using an instrument of the invention and retrieving information from the instrument of the invention about the date of the detection of the infection, whereby a date after the hospital admittance date and an incubation period shorter than the current hospital stay, is indicative of a nosocomial infection.

In yet another aspect, the invention provides for a method to control an infection in an individual or an environment without the need for prior taxonomic classification of the microorganism(s) in the sample of interest. This method comprises classifying a microorganism in a sample of interest using an instrument of the invention; retrieving information from the instrument of the invention about the microorganism and taking appropriate measure to control the infection.

Since the method of the invention is quick and straightforward, and relatively simple to perform, it may suitably be used for the automated detection of hospital outbreaks, i.e. when a significant (abnormally high) number of patients acquire infections within a short period of time, without there even being a prior suspicion of an outbreak and without requiring additional measurements or tests i.e. other than those already performed to determine the best course of treatment for the individual patient of which the isolate was obtained. An outbreak may be detected without prior suspicion of an outbreak and without requiring prior taxonomic classification of the microorgansim involved by classification of a microorganism in a sample of interest using the instrument according to the invention. Then, determining the numbers of samples from different individuals with a specific infection over a certain period of time, whereby the finding of a larger-than-expected number of samples of a specific infection is indicative of an outbreak.

The method of the invention also allows for the tracing of a source of microbial infection or of contamination since it allows for the rapid determination of re-infection of a patient with the same strain. On the other hand, it can also prevent costly hygienic measures being taken if e.g. two methicillin-resistant *Staphylococcus aureus* (MRSA) infections are encountered on the same day, which are not caused by the same strain The method of the invention also allows for the monitoring of strain prevalence, since it gives information on earlier cases of infection with the same strain. An unusual prevalence of such infections points to a strain having colonized the hospital. This is detected automatically without any requirement for further tests. At the same time it provides information regarding earlier cases of infection with the same strain and can send out an alert if such an infection was found within a certain (user-defined) prior time frame. No further separate/specific testing to establish such is needed. The method of the invention may also advantageously be used for monitoring changes in antibiograms at any geographical scale.

The person skilled in the art will understand that the method of the invention allows for the tracing of the source of contamination in many types of industry, particularly in the food industry, cosmetics industry and pharmaceutical industry. It is noted that the instrument and method of the invention may also be used in situations were microrganisms are produced on purpose, e.g. in fermentation processes or in probiotic nutrition treatments using microorganisms. In these situations, the microorganisms is very likely not eliminated, but on the contrary, the instrument is used to make sure that the microorganism is present and stays present and adequate warnings should then be given to indicate that the organism has been lost or that spectral characteristics of the organism have changed.

EXAMPLES

Example 1

Sample Preparation

The microorganism strains that were used in the experiment are listed in Table 1. The strains, stored at −80° C. in a brain-heart infusion broth (Becton Dickinson, Franklin Lakes, N.J., USA) containing 10% glycerol were thawed and cultured overnight (~16-20 hours at 37° C.) on Mueller-Hinton (MH) medium (Merck, Darmstadt, Germany). Then biomass from colonies growing on the medium was collected with a 1 mm platinum loop and transferred onto a $CaF_2$ window of 25×40 mm and 1 mm thick. 25 smears were loaded of approx. 5 mm in length and 2 mm in width, in a 5×5 matrix.

Example 2

Raman Measurements

Raman spectra were acquired using a Renishaw System 1000 Raman microspectrometer (Renishaw plc, Gloucestershire, UK). The Leica DM-LM microscope, which forms the microscope part of the Renishaw system was fitted with an 80× near-infrared objective (MIR Plan 80×/0.75, Olympus). The entrance slit width of the spectrometer was set to 30 µm. The spectrometer was equipped with a 300 lines/mm grating. Raman signal was collected in the spectral interval from 250 cm$^{-1}$ to 2150 cm$^{-1}$, with a spectral resolution of about 8 cm$^{-1}$. Raman measurements were performed using 830 nm excitation from a titanium sapphire laser (model 3900, Spectra Physics, Mountain View, Calif., US) pumped by an argon-ion laser (series 2000, Spectra Physics, Mountain view, Calif., US), delivering 100 mW of laser power on the sample.

The bacteria smears were placed under the microscope objective in the laser focus. At random locations in each smear, ten-spectra were collected, each with a 30-s signal integration time. The 10 spectra thus obtained were separately used in further analysis.

The spectral database is constructed of spectra of eleven bacterial species (see Table 1), divided over three genera. The outbreak strains of the genus *Acinetobacter*, were previously described by Dijkshoorn et al (1993) J Clin Microbiol 31:702 Four methods, namely, biotyping, cell envelope protein electrophoresis, ribotyping, and comparison of antibiograms, were used for strain identification of the isolates from five outbreaks in hospitals. For each strain, ten spectra were included, collected from 10 different locations in the smear on CaF$_2$ (see microbiology and sample treatment). For all the strains belonging to the genus *Enterococcus*, two repeated cultures were prepared from the −80° C. stock cultures. Moreover, from each culture two independent smears were prepared, leading to a total of 40 spectra per strain.

Example 3

Spectrum Pre-Treatment Before Analysis

Prior to subjecting the measured spectra to the algorithm for strain identification the spectra were pretreated as follows. The constant background signal contribution originating from optical elements in the laser light delivery pathway was subtracted from all spectra. Both the wavenumber and intensity axis of the spectra were calibrated. The wavenumber range that was projected on the CCD-camera was determined by measuring the spectra of two calibration lamps of which the absolute peak positions are known (a neon-lamp and a neon-argon-lamp) and one or more Raman standards of which the relative positions of the Raman peaks have been precisely determined (e.g. cyclohexane, 4-aceto-amidophenole). First a third order polynomial was fitted through the absolute calibration points (peak positions in nanometers as a function of the pixel numbers) to yield an absolute wavelength axis. Then the relative positions of the Raman peaks were used to calculate the exact laser wavelength. From the absolute wavelength axis and the laser wavelength the relative wavenumber axis was determined. This results in accuracy of the wavenumber axis of about a tenth of the pixel-width in wavenumbers, i.e. about 0.3 wavenumbers.

The reference spectrum of a tungsten band lamp of known temperature was used to correct for the wavelength dependent signal detection efficiency of the Raman set-up. The spectrum of the band lamp was calculated from Planck's radiation law and the emissivity of tungsten. The ratio of the measured spectrum and the calculated spectrum gave the instrument response profile which was used to correct all measured spectra.

All spectra were then filtered using a 9-point Savitsky Golay filter, in which the first derivative of the spectrum is calculated. The spectral region between 400 and 1800 wavenumbers was used for data analysis. Finally each spectrum

TABLE 1

Microorganisms strains used in experiment

| Genus | Species | Number of strains | number of spectra | Ref. | remarks |
|---|---|---|---|---|---|
| Enterococcus | faecalis | 6 | 240 | (2) | |
| | faecium | 5 | 200 | (2) | |
| | Hirae | 2 | 80 | (2) | |
| | Durans | 2 | 80 | (2) | |
| | casseliflavus | 1 | 40 | (2) | |
| | gallinarum | 2 | 80 | (2) | |
| Staphylococcus | Aureus | 20 | 200 | (3) | |
| Acinetobacter | DNA group 3 | 1 (5 isolates) | 50 | (1) | isolates from an outbreak in The Hague, The Netherlands |
| | DNA group 13 | 1 (5 isolates) | 50 | (1) | isolates from an outbreak in Odense, Denmark |
| | baumannii | 1 (5 isolates) | 50 | (1) | isolates from an outbreak in Venlo, The Netherlands |
| | | 1 (5 isolates) | 50 | (1) | isolates from an outbreak in Basildon, UK |
| | | 1 (5 isolates) | 50 | (1) | isolates from an outbreak in Newcastle, UK |
| | baumannii | 4 | 40 | (1) | sporadic/independent strains |
| Total | | 67 | 1210 | | |

(1) Dijkshoorn et al.(1993) J Clin Microbiol 31: 702.
(2) Kirschner, C. et al. (2001).. J Clin Microbiol 39: 1763.
(3) van Leeuwen, W et al.(2001). J Clin Microbiol 39: 328.
(4) Wolthuis, R., et al. (1999)., p. 431. In W. T. Mason (ed.), Fluorescent and luminescent probes for biological activity, 2nd ed. Academic press, London.

was scaled by subtracting the overall mean of the spectrum (i.e. the average signal of all spectral measurement channels) and dividing the spectrum by its overall standard deviation (a method commonly referred to as Standard Normal Variate scaling).

Example 4

Signal Analysis

The division of the spectra in this database over spectral subspaces by the unsupervised classification method is accomplished by 4 automatically generated LDA-models in 2 hierarchical levels that split up the database in 18 subspaces. The largest subspace consists of 240 spectra, the smallest of 20 spectra.

Three tests were performed to check the ability of the invention to automatically detect an outbreak of infections caused by a microbial strain. To this end an initial classification model was created based on the database described in table 1 from which the spectra of one of the sporadic *A. baumanii* strains were omitted, as well as the spectra of one of the isolates of the DNA-group 3 outbreak and the spectra of all isolates of the Newcastle outbreak.

Three tests were performed which simulate practical situations:

a) The spectra of a single sporadic strain of *A. baumannii* were presented to the model. This examples serves to analyse the results obtained when spectra of a strain are analyzed that has not been encountered before.
b) Next, the spectra of the *A. baumannii* isolate from the DNA group 3 outbreak that had been omitted from the spectral database, were presented to the classification model, with the spectra of the four epidemiologically related other *A. baumannii* isolates already included in the spectral database. This simulates the situation during an outbreak, when a new outbreak isolate is encountered.
c) Finally, the spectra of the *A. baumannii* isolates of the Newcastle outbreak were presented to the model. Of none of the five isolates spectra were included in the spectral database. The spectra of each of these five isolates were then presented to the classification model. Thus the situation at the start of an outbreak is simulated.

Example 4a

In the first test the spectrum of a sporadic *A. baumannii* strain, of which no spectra were present in the database was presented to the classification model. It was recognised by the LDA models as belonging to a spectral subspace with only *A. baumannii* strains. However, within this cluster spectral similarity with any of the spectra already in the database was not sufficient to allow spectroscopic identification of the isolate. The classification model classified the isolate as unknown and prompted the user to supply information about this strain. The spectrum was then automatically added to the database. The remaining nine spectra obtained from the same isolate were subsequently presented to the classification model and were all correctly spectroscopically identified as the newly added strain, with the information supplied by the user becoming available.

Example 4b

In the second test, the spectra of an *A. baumannii* isolate were analysed, which belonged to the Basildon outbreak. The spectra of four other independent isolates of this outbreak-strain obtained from different patients were already in the database. The first LDA-model of the analysis, assigned the spectra to a subgroup containing only *Acinetobacter* strains. A second LDA-model classified the spectrum as belonging to the spectral subspace occupied by only *A. baumannii* strains from the Basildon and Venlo outbreaks. The cluster analysis on this spectral subspace showed that the spectra of the isolate were all sufficiently similar to spectra of Basildon outbreak isolates already in the database, to identify the new isolate as the Basildon outbreak strain.

Example 4c

In the third test the spectra obtained from the five isolates of the Newcastle outbreak were analyzed by the classification model and added to the database one-by-one. The first LDA-model classified the first Newcastle outbreak spectrum presented to it, as belonging to a group with only *Acinetobacter* strains. The LDA-model which further subdivided this group, classified the spectrum as belonging to the spectral subspace which also contains the spectra of isolates of two other independent outbreaks (namely the Basildon outbreak and the Venlo outbreak). However, the result of the cluster analysis carried out on this spectral subspace including the new spectrum, showed that the spectral similarity between the new spectrum and any of the spectra already present was not sufficient for identification. The spectrum was added to the spectral database in the spectral subspace it was assigned to by the LDA-models, and the user was prompted to provide information about this isolate to the information database. The other spectra of this isolate and of the other four isolates obtained from this outbreak strain were subsequently immediately identified as this new entry. This illustrates how the invention can be used to automatically detect an outbreak of infections caused by a still unknown strain. The information entered in the information database could in principle be limited to a code-name for an unknown strain. The spectroscopic taxonomy system of the invention would nevertheless automatically alert the user of an outbreak when other isolates contain the same strain.

The invention claimed is:
1. A method for detection of an outbreak without prior suspicion of an outbreak and without requiring prior taxonomic classification, which method comprises:
obtaining vibration spectrum for a microorganism in a sample of interest using an instrument comprising a vibrational spectrometer, a processing means, a first spectral database (10) and a first information database (200), for obtaining information about the microorganism in the sample of interest;
classifying the microorganism in the sample of interest based on the obtained vibration spectrum and without requiring prior taxonomic classification, the classification being performed by establishing vibrational spectroscopic similarity of the obtained vibrational spectrum of the microorganism in the sample of interest to a vibrational spectrum of a microorganism that is present in the first spectral database, and the microorganism in the sample of interest being not yet represented in the first spectral database if no vibrational spectroscopic similarity is established;
adding the obtained vibration spectrum to the first spectral database for classifying subsequent microorganisms in a sample of interest;
adding information about time and place of isolation of the microorganism in a sample of interest and information about an object or an individual from which the microorganism was isolated to the first information database; and determining the number of samples of interest obtained from different objects or individuals with the same microorganism over a certain period of time, the finding of a greater than normal number of samples of interest of the same microorganism being indicative of an outbreak, wherein, the vibrational spectrometer, for determining a vibrational spectrum (160) of the microorganism in the sample of interest, is linked to the processing means;

the processing means, for both (i) executing a computer program which comprises computer executable software code for analysis of the signal obtained from the spectrometer and (ii) for classification (190) of the microorganism in the sample of interest, is linked to the spectrometer and to the databases (10) and (200);

the first spectral database (10), which comprises zero or more vibrational spectra of microorganisms for establishing similarity of the spectrum of the microorganism in the sample of interest to the vibrational spectrum of a microorganism of which the spectrum is present in the first spectral database (10), is linked to the processing means; and the first information database (200) is linked to the processing means.

2. The method according to claim 1 wherein the sample of interest is part of (i) a colony of biomass which was grown on a solid culture medium or (ii) a concentrated pellet from a liquid culture medium which was transferred to carrier material without further preparation.

3. The method according to claim 1 wherein the processing means is a computer which is linked to other computers in a local or global network.

4. The method according to claim 1 wherein the instrument further comprises:

a second spectral database which comprises vibrational spectra which are not present in the first spectral database, and a second information database which comprises additional information about times and places of isolation of samples of interest which included the microorganisms, and information about objects or individuals from which the microorganisms were isolated, of the second spectral database.

5. The method according to claim 1, which further comprises generation of a signal, which is or can be made visible or audible, in one or more of the following categories:

prompting the user to enter information in a second information database, and alerting the user to the existence of an outbreak.

6. The method according to claim 1 wherein the instrument self generates an algorithm for establishing similarity of the spectrum of the microorganism in the sample of interest to the spectrum of the microorganism that is present in the first spectral database.

7. The method according to claim 6 wherein a computer is not linked to a first spectral database but, in operation, is executing an algorithm based on the first spectral database.

8. The method according to claim 1 further comprising forming a second spectral database or an algorithm based on the first spectral database and the first information database combined together.

9. The method according to claim 1 wherein the spectrometer is a Raman spectrometer and the spectrum obtained is a Raman spectrum.

10. The method according to claim 1 wherein the sample of interest is patient material obtained from an individual or the sample of interest is obtained from an object selected from the group consisting of a medical instrument, an industrial production line, a water system, a food product, a cosmetic product and a pharmaceutical product.

11. The method according to claim 1 wherein the microorganism in the sample of interest is a member of any of the following genera:

*Staphylococcus, Enterococcus, Mycobacterium, Acinebacter, Streptococcus, Pseudomonas, Salmonella, Escherichia.*

12. The method according to claim 1 wherein the classification of the microorganism by vibrational spectrum and the additional information is at either a species or strain level.

13. A method for detection of an infection with an endemic microorganism, i.e. a microorganism which is endemic to a hospital, and without requiring characterizing data of the microorganism involved, which method comprises:

obtaining vibration spectrum for a microorganism in a sample of interest using an instrument comprising a vibrational spectrometer, a processing means, a first spectral database (10) and a first information database (200), for obtaining information about the microorganism in the sample of interest;

classifying the microorganism in the sample of interest based on the obtained vibration spectrum so that characterizing data of the microorganism in the sample of interest is not required, the classification being performed by establishing vibrational spectroscopic similarity of the obtained vibrational spectrum of the microorganism in the sample of interest to a vibrational spectrum of a microorganism that is present in the first spectral database;

adding the obtained vibration spectrum to the first spectral database for classifying subsequent microorganisms in a sample of interest; and determining the number of samples from different individuals or places with a specific infection over a certain period of time, whereby the finding that a specific infection is localized in a hospital is indicative of an infection with an endemic strain, wherein, the vibrational spectrometer, for determining a vibrational spectrum (160) of the microorganism in the sample of interest, is linked to the processing means;

the processing means, for executing a computer program which comprises computer executable software code for analysis of the signal obtained from the spectrometer and for classification (190) of the microorganism in the sample of interest, and is linked to the spectrometer and to the databases (10) and (200);

the first spectral database (10), which comprises zero or more vibrational spectra of microorganisms for establishing similarity of the spectrum of the microorganism in the sample of interest to the vibrational spectrum of a microorganism of which the spectrum is present in the first spectral database (10), is linked to the processing means; and the first information database (200), which contains additional information about times and places of isolation of samples of interest which included the microorganisms, and information about individuals or places from which the microorganisms were isolated, of which the spectrum is present in the first spectral database (10), is linked to the processing means.

14. A method for detection of a re-infection with the same microorganism, and without requiring characterizing data of the microorganism involved, which method comprises:

obtaining vibration spectrum for a microorganism in a sample of interest using an instrument comprising a vibrational spectrometer, a processing means, a first spectral database (10) and a first information database (200), for obtaining information about the microorganism in the sample of interest;

classifying the microorganism in the sample of interest based on the obtained vibration spectrum so that characterizing data of the microorganism in the sample of interest is not required, the classification being performed by establishing vibrational spectroscopic similarity of the obtained vibrational spectrum of the microorganism in the sample of interest to a vibrational spectrum of a microorganism that is present in the first spectral database;

adding the obtained vibration spectrum to the first spectral database for classifying subsequent microorganisms in a sample of interest; and determining whether the microorganism matches with a microorganism which was obtained from a previous sample from the same source, whereby the finding of a matching microorganism is indicative of a re-infection with the same strain, wherein, the spectrometer, for determining a vibrational spectrum (160) of the microorganism in the sample of interest, is linked to the processing means;

the processing means, for executing a computer program which comprises computer executable software code for analysis of the signal obtained from the spectrometer and for classification (190) of the microorganism in the sample of interest, is linked to the spectrometer and to the databases (10) and (200);

the first spectral database (10), which comprises zero or more vibrational spectra of microorganisms for establishing similarity of the spectrum of the microorganism in the sample of interest to the vibrational spectrum of a microorganism of which the spectrum is present in the first spectral database (10), is linked to the processing means;

the first information database (200), which contains additional information about times and places of isolation of samples of interest which included the microorganisms, and information about a source from which the microorganisms were isolated, of which the spectrum is present in the first spectral database (10), is linked to the processing means.

* * * * *

UNITED STATES PATENT AND TRADEMARK OFFICE
CERTIFICATE OF CORRECTION

PATENT NO. : 8,688,384 B2
APPLICATION NO. : 10/556365
DATED : April 1, 2014
INVENTOR(S) : Puppels et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1037 days.

Signed and Sealed this
Twenty-ninth Day of September, 2015

Michelle K. Lee
*Director of the United States Patent and Trademark Office*